Feb. 28, 1967 S. McGREDY Plant Pat. 2,721
ROSE PLANT
Filed Oct. 22, 1965
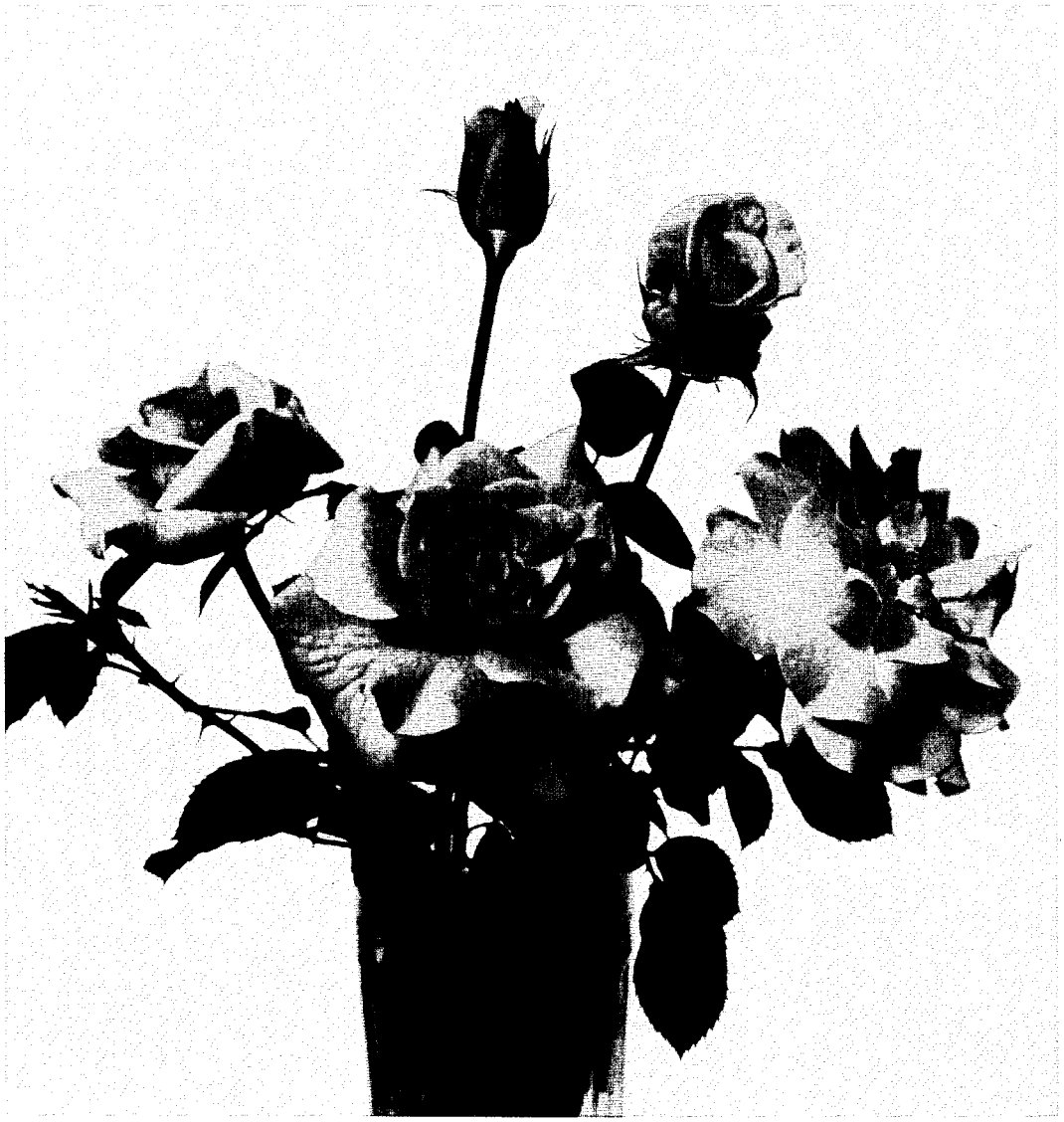

United States Patent Office

Plant Pat. 2,721
Patented Feb. 28, 1967

2,721
ROSE PLANT
Samuel McGredy, Portadown, Northern Ireland
Filed Oct. 22, 1965, Ser. No. 502,785
1 Claim. (Cl. Plt.—27)

The invention relates to a new and distinct variety of rose plant of the floribunda class, originated by me in April 1957, as a consequence of a breeding program begun in 1957. The parentage of my new rose plant is as follows: Spartan Pl. Pat. No. 1,357, the seed parent × Highlight, the pollent parent.

The object of the cross was to raise a free flowering floribunda rose with the constitution of the female parent, Spartan, but with a high centered hybrid tea type bud combined with a pastel coral-salmon color similar to that seen in the variety "Fashion" Pl. Pat. No. 789. These objectives were achieved along with other desirable improvements, as evidenced by the following unique combination of characteristics which are outstanding in the new variety and which distinguish it from its parent as well as from all other varieties of which I am aware. My new variety is primarily characterized by:

Its vigorous upright plant habit; its habit of growth in which the plant retains an average height of about three feet; its continuity of bloom; its habit of bearing medium clusters of long lasting flowers which are particularly resistant to wet weather conditions; its distinctive and attractive color tonality of the flowers corresponding to a pastel coral-salmon and which is much more striking than that found in older varieties; and the strong fragrance of the blooms.

Asexual reproduction of my new variety by budding, through a series of annual propagations at Portadown, Northern Ireland; Hemet, California; Wilsonville, Oregon; Livermore, California, shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container grown budded plants under greenhouse and field conditions at Santa Rosa, California.

Tall vigorous, upright plant, robust but refined in appearance. New canes are regularly produced from the base of the plant maintaining a full, compact, yet uncrowded habit of growth. Mature garden specimens 30"–40" tall by 25"–35" wide. General habit subfastigiate with all primary canes strongly ascending. Young primary canes from ¼"–⅝" in diameter proximally, reddish-purple when young, green when mature, armed. The thorns are strong, stout at the bases, slender distally, extremely sharp, needle-like. The bases of the thorns variable about ⅛"–5/16" tall by 1/32"–⅛" wide, about 5/16"–⅜" long, slightly recurved, but not hooked, with the point halfway below the midpoint of the base, the larger sizes predominating. The young thorns red, semi-translucent, with essentially white tips, becoming lighter with age. The mature thorns tan to straw, opaque.

The foliage, large, dark green, glossy, leathery, reddish when young, especially below (Purple Madder HCC 1028/3); mature leaves, Lavender Green (HCC 00761) below, Ivy Green (HCC 000 1060/3) above. Leaflets 3–7 mostly 5, unequal in size, increasing in size distally with the terminal leaflet largest. Average leaf about 5" long by 3½" wide. The rachis of the leaf is sparsely armored below, grooved and glabrous above. The leaflets vary from about ⅞" long by 9/16" wide to about 2⅛" long and 1⅝" wide; the margins of the leaflets essentially simply serrate. The serrations are coarse.

The inflorescence is a 1–3 flowered determinate corymb, subtended by bracts and/or reduced leaves. The bracts are linear, ligulate, rarely inconspicuously lobed, or serrate-ciliate. The transition from leaves to bracts is abrupt. The terminal flower is larger than the laterals. Peduncles stout 2"–2½" long, with moderate short, reddish prickles. The base of the hypanthium is glabrous.

The flower is large 3"–4" across, fragrant, of classical hybrid tea form, high centered and fully double. The sepals are somewhat ornate along their margins, but the tips of the sepals are acute, lanceolate and entire. The sepals are about 7/16" wide at the base and 1 3/16" long. The petals are circular in outline with wavy margins about 1⅝" by 1⅝". The petals are essentially unclawed 20–25 with 12–20 staminodes. The petals are light Mandarin Red (HCC 17–1) to Porcelain Rose (HCC 620) underlain with Buttercup Yellow (HCC 5/1) appearing pastel coral-salmon to the eye, with a buttercup yellow eye about ¼" across by 3/16" long. The old petals are Geranium Lake (HCC 20/2) to Rose Madder (HCC 23/3), appearing warm rose-pink to the eye. Stamens abundant, 100–130 with red filaments. Pistils numerous, about 75–100. The styles red above, white below, the stigmas white. The ovaries are ordinary. The variety is highly fertile forming many fruits yellow-orange to orange red, essentially spheroid, about ¾" in diameter. The sepals persist but become dry and break off usually before the fruit matures.

Having thus disclosed my invention, I claim:

A new and distinct variety of rose plant of the floribunda class primarily characterized by: its vigorous upright plant habit; its habit of growth in which the plant retains an average height of about three feet; its continuity of bloom; its habit of bearing medium clusters of long lasting flowers which are particularly resistant to wet weather conditions; its distinctive and attractive color tonality of the flowers corresponding to a pastel coral-salmon and which is much more striking than that found in older varieties; and the strong fragrance of the blooms.

No references cited.

ABRAHAM G. STONE, *Primary Examiner.*

R. E. BAGWILL, *Assistant Examiner.*